United States Patent [19]

Yelderman et al.

[11] Patent Number: 5,159,936
[45] Date of Patent: Nov. 3, 1992

[54] NONCONTACT INFRARED TYMPANIC THERMOMETER

[76] Inventors: Mark Yelderman, 5205 Terrace View Rd., Plano, Tex. 75093; Daniel S. Goldberger, 1035 Douglas St., San Francisco, Calif. 94114; James R. Braig, 6147 Chelton Dr., Oakland, Calif. 94611

[21] Appl. No.: 570,205

[22] Filed: Aug. 17, 1990

[51] Int. Cl.$^5$ ............................. A61B 5/00; G01J 5/10
[52] U.S. Cl. .................................... 128/736; 128/664; 374/126; 374/158
[58] Field of Search ................ 128/736, 664; 374/120, 374/121, 126, 158, 179, 181

[56] References Cited

U.S. PATENT DOCUMENTS

| | | | |
|---|---|---|---|
| 3,282,106 | 11/1966 | Barnes et al. | 73/355 |
| 3,662,360 | 5/1987 | O'Hara et al. | 128/9 |
| 3,878,836 | 4/1975 | Twentier | 128/9 |
| 4,380,998 | 4/1983 | Kieffer, III et al. | 128/9 |
| 4,602,642 | 7/1986 | O'Hara et al. | 128/664 |
| 4,722,612 | 2/1988 | Junkert et al. | 374/124 |
| 4,784,149 | 11/1988 | Berman et al. | 128/664 |
| 4,790,324 | 12/1988 | O'Hara et al. | 128/664 |
| 4,797,840 | 1/1989 | Fraden | 364/557 |
| 4,895,164 | 1/1990 | Wood | 128/736 |
| 4,900,162 | 2/1990 | Beckman et al. | 374/132 |
| 4,932,789 | 6/1990 | Egawa et al. | 374/126 |

OTHER PUBLICATIONS

C. Hamel, "Noncontact Temperature Sensing With Thin Film Thermopile Detectors", *Sensors*, Jan. 1989, pp. 28-32.

L. A. Hancock, "FirstTemp", *Journal of Pediatric Health Care*, May-Jun. 1987, vol. 1, No. 3, p. 163.

*Primary Examiner*—Lee S. Cohen
*Assistant Examiner*—Kevin Pontius
*Attorney, Agent, or Firm*—Woodcock Washburn Kurtz Mackiewicz & Norris

[57] ABSTRACT

A noncontact infrared tympanic thermometer which does not require environmental stabilization or waveguide temperature control because it utilizes an optically stabilized infrared detector for detecting the infrared energy emitted by the tympanic membrane. The optical stabilization renders the instrument insensitive to ambient temperature effects and allows it to read true tympanic membrane temperatures unaffected by the temperature of the side walls of the detector package. This selectivity is accomplished by locating a neutral density filter over half of the optical aperture of the detector package such that the neutral density filter "shadows" only one of two thermopile channels for detecting the infrared energy emitted by the tympanic membrane. The two thermopile channels are connected in series opposition such that any optical signal equally present in both channels will yield a zero net output. Since the infrared energy emitted by the walls of the detector package reach each detector equally, the effects of these emissions on the temperature measurement are eliminated. The neutral density filter prevents the energy from the tympanic membrane from falling equally on the two thermopile detectors and similarly cancelling. Instead, the resulting differential signal may be processed along with the ambient temperature signal to determine the temperature of the tympanic membrane. The infrared detector of the invention may also be incorporated into an otoscope.

21 Claims, 3 Drawing Sheets

TYMPANIC THERMOMETER 10

NONCONTACT INFRARED TYMPANIC THERMOMETER

BACKGROUND OF THE INVENTION

1. Field of the Invention

The present invention relates to a device for measuring temperatures by quantifying infrared emissions, and more particularly, to a device which measures patient body temperature by quantifying the infrared emissions from the tympanic membrane.

2. Description of the Prior Art

The tympanic membrane has long been known to be an excellent spot to check body temperature because it shares the blood supply that reaches the hypothalamus, the center of core body temperature regulation. Also, the ear is generally considered to be a more acceptable site than the mouth or rectum for temperature measurement, for use of the external auditory canal eliminates common problems such as breakage or perforation of the rectal wall or biting or gagging on a probe placed in the mouth. As early as the 1960's, thermistors in contact with the tympanic membrane were routinely used in the treatment of severely burned patients. However, because of the risk of injury and inconvenience of application, such contact type temperature sensors have not been widely used to measure temperatures in the ears of awake, alert patients.

Noncontact infrared thermometry differs from the above-referenced contact thermometry in that a sensor is placed at the external opening of the auditory canal for sensing the infrared energy emitted from the tympanic membrane, without contacting the tympanic membrane. Noncontact infrared thermometry is routinely used in industry to remotely measure process and machinery temperatures, and techniques for this purpose are described in detail in an article by C. Hamel entitled "Noncontact Temperature Sensing With Thin Film Thermopile Detectors," SENSORS, Jan. 1989, pages 28-32. However, although noncontact infrared thermometry is common in industrial applications, this technology has only recently been applied to medical temperature measurements.

In clinical application, the end of the probe portion of a noncontact infrared sensor must be small enough to be placed in the outer portion of the auditory canal (just past the cartilage of auricula), where the sensor can get a clear "view" of the tympanic membrane. Placing such a sensor requires only a little training and is very similar to the maneuver used to visualize the eardrum with an otoscope. Typically, there is no risk of eardrum injury because the probe is not long enough or small enough to be inserted past the mastoid process. Moreover, normal amounts of cerumen (ear wax) in the auditory canal typically do not interfere with an accurate temperature reading.

The most advantageous feature of infrared tympanic thermometry is that it takes very little time. Temperature readings typically can be taken in a few seconds. Speed is inherent in infrared thermometry because the sensors measure emitted infrared radiation instead of being brought into contact with the body until thermal equilibrium is reached as with typical oral thermometers. The speed means less discomfort to patients, which is especially important for children and in emergency situations. Another widely appreciated advantage over conventional thermometers is that tympanic thermometry uses the ear, which is less likely to harbor pathogens than the mucous membrane-lined mouth or rectum.

An early device for such a method of measuring body temperature using infrared emissions from the tympanic membrane is disclosed by Barnes in U.S. Pat. No. 3,282,106. Barnes therein discloses the general configuration of a tympanic membrane directed infrared thermometer which is inserted into the auditory canal so as to sufficiently enclose the detector apparatus such that multiple reflections of the radiation from the tympanic membrane transform the auditory canal into a "black body" cavity, a cavity with emissivity theoretically equal to one. However, in his early example of a noncontact infrared tympanic thermometer, Barnes does not consider, or in any way describe, how the device of that patent is calibrated, how accuracy is maintained for clinical use, or how contamination of the instrument by cross-infection can be prevented. Such problems have restricted the usefulness of the tympanic thermometer of Barnes in clinical settings.

Subsequent patents have addressed the problems with the thermometer of Barnes. For example, O'Hara et al. describe in U.S. Pat. Nos. 4,602,642 and 4,790,324 a noncontact infrared tympanic thermometer which addresses the calibration issues left unexplored by Barnes. In fact, the infrared sensor of O'Hara et al. is calibrated before each use. For this purpose, the sensor is housed in a temperature controlled cavity and special care is taken to maintain a constant temperature in the waveguide which directs the infrared emissions from the tympanic membrane onto the detector. In particular, the hand held probe unit of the tympanic thermometer of O'Hara et al. has an infrared sensitive thermopile mounted in a metal housing which is kept at a constant reference temperature by a regulator circuit. A waveguide tube surrounded by a thermally insulative probe directs infrared emissions from the tympanic membrane to the thermopile. The thermopile and regulator circuit of the probe unit are then electrically connected to a processing circuit in a chopper unit. Prior to taking a patient's temperature, the probe unit is mated with the chopper unit so that the thermopile detects infrared emissions from a reference target which is also kept at a constant reference temperature by another regulator circuit. The processing circuitry repeatedly acquires the output level of the thermopile and stores calibration data. The probe unit is then removed from the chopper unit, the probe is covered with an infrared transparent disposable speculum and is inserted into the patient's external ear canal. The patient's core temperature is then determined by comparing the stored calibration data to the maximum output of the thermopile during a succession of auditory canal samplings.

Another technique for calibrating a noncontact infrared thermometer is disclosed by Berman et al. in U.S. Pat. No. 4,784,149. Berman et al. therein disclose an automatic calibration technique for an infrared thermometer whereby the housing of the device is provided with a chamber shaped to receive the probe and a target for viewing by the infrared sensor when the probe is in the chamber. An error signal is thereby generated which is added to the output signals of an ambient temperature sensor and an infrared sensor within the probe when they view a body tissue for temperature measurement.

Fraden discloses in U.S. Pat. No. 4,797,840 a further calibration technique for an infrared thermometer in which a pyroelectric sensor in the thermometer housing is shielded from infrared radiation from exterior to the thermometer housing and is then selectively exposed to infrared radiation from the object to be measured to generate a first electrical signal related to the absolute temperature of the object to be measured. The ambient temperature of the pyroelectric sensor is then sensed and a second electrical signal proportional thereto is generated. The first and second electrical signals are then processed to calculate the temperature of the object to be measured. Errors due to temperature differences are minimized by thermally isolating the barrel of the sensor (which is in thermal equilibrium with the pyroelectric sensor) from ambient heat sources such as the human body by a protective thermoisolator coating. Calibration is accomplished by electrical calibration using a calibration circuit (FIG. 9) including a piezoelectric element which creates a mechanical stress calibration signal when a shutter is closed. The value of the electrical signal at the time of calibration of the thermometer is stored in memory. The shutter is then opened for temperature readings, and the resulting reading is adjusted by the stored value.

Wood discloses in U.S. Pat. No. 4,895,164 a technique for maintaining accuracy in clinical settings when using a noncontact infrared tympanic thermometer. During use, the radiation sensor is held in isothermic condition with a waveguide at ambient temperature. A thermistor or some other temperature sensor is thermally coupled to the radiation sensor for compensating for changes in ambient conditions. Also, the infrared radiation sensor of the device of Wood is constructed and configured so as to remain in an isothermic state, even during changes of ambient temperature, by positioning the infrared radiation sensor assembly within the housing so as to form an insulative air space between the housing wall and the isothermic assembly. Low emissivity barriers such as polished or gold plated aluminum tubing are also placed around the protruding portion of the waveguide in order to insulate the waveguide to limit the effects of temperature changes. Thus, accuracy is maintained in the device of Wood by maintaining a thermally stable environment around the detector.

On the other hand, Beckman et al. disclose in U.S. Pat. No. 4,900,162 a radiometer thermometry system for measuring the temperature of a target such as a tympanic membrane in which the temperature of the radiation detector can be changed so as to minimize the difference between the temperature of the target (tympanic membrane) and the temperature of the radiation detector (ambient temperature). The target temperature is thus detected by a sort of successive approximation (null seeking) technique. A related technique is taught by Egawa et al. in U.S. Pat. No. 4,932,789, who teach preheating the probe to a reference temperature close to normal body temperature despite the ambient temperature.

Junkert et al. disclose in U.S. Pat. No. 4,722,612 an attempt to stabilize the detector rather than the detector's environment. In the device of Junkert et al., an optical blocking baffle is placed over one-half of a two element pair so as to render that half insensitive to incoming radiation. The thermopile detectors are connected in series opposition and adjacent to each other. Both detector halves are sensitive to ambient temperature, and since only one detector is sensitive to incoming radiation, the Junkert et al. detector is "stabilized" against some ambient temperature fluctuations. However, by totally blocking the radiation falling on a portion of the detector in this manner, Junkert et al. cause a temperature gradient to be generated in the detector substrate, thereby inducing errors. Moreover, by blocking radiation at the substrate level, unwanted radiation from the walls of the detector package is not eliminated and thus causes further errors.

Devices for preventing contamination of a tympanic thermometer because of the accumulation of ear wax and the like are also known. For example, O'Hara et al. disclose in U.S. Pat. No. 4,662,360 a protective, disposable speculum for use with an infrared tympanic thermometer. The device includes an infrared transparent window and method for manufacturing it in a manner that would insure repeatable infrared transmission properties through the window, for if the transmission properties vary from unit to unit the calibration of the instrument would not be stable. Since the device is disposed of after each use, cross-contamination by ear wax and the like is avoided. Another example of a disposable speculum is disclosed by Twentier in U.S. Pat. No. 3,878,836, while a speculum for use with an otoscope is described by Kieffer, III et al. in U.S. Pat. No. 4,380,998.

Although prior art infrared thermometers of the type described above have addressed many of the shortcomings of the Barnes thermometer, several problems remain. For example, since the prior art noncontact infrared thermometers propose to maintain accuracy primarily by maintaining a thermally stable environment around the detector during operation, their accuracy is limited by the ability to maintain isothermic conditions in areas where there may be substantial temperature differences. In other words, since the environment around the detectors may not be made truly isothermic, more accurate detectors which need not be maintained under such conditions and which do not induce temperature gradients are desired for clinical use.

Reliable infrared detector devices which are extremely accurate in clinical use have been previously developed by the present inventors for use in a capnograph. As described in our U.S. Pat. application Ser. No. 07/401,952 (abandoned), 07/522,208 and 07/522,177 (now U.S. Pat Nos. 5,095,913 and 5,081,998, respectively), we have previously developed a detector device which eliminates thermal drift of thermopile detectors used in detecting the concentration(s) of at least one gaseous component of gases expired by a patient. The apparatus described in those applications comprises at least two series opposed infrared detectors which generate electrical signals when illuminated by optical energy provided by an infrared radiation source. In other words, the detectors are connected so that their outputs are subtracted. Outputs from the detectors are thus possible only if the same energy does not fall equally on both detectors. For this purpose, means for attenuating the infrared energy illuminating at least one of the detectors is provided. An optically stabilized signal is thereby produced since the undesired infrared signals fall upon both detectors equally and are effectively cancelled out, while the desired signal is maintained because of the difference provided by using the attenuating means over one of the optical detectors. The resulting information may then be processed and displayed as representative of the concentration of elements such as $CO_2$ expired by a patient. However, no such technique has previously been used to overcome the above-mentioned problems with noncontact infrared thermometers so as to permit more widespread clinical use of such devices.

Accordingly, it is desired to overcome the aforementioned problems with prior art noncontact infrared tympanic thermometers by utilizing optically stabilized infrared detectors. The present invention has been designed to adapt our above-mentioned optical stabilization techniques into noncontact infrared tympanic thermometers so as to improve their accuracy without adversely affecting their ease of use.

SUMMARY OF THE INVENTION

The present invention relates to a noncontact infrared tympanic thermometer which utilizes the optical stabilization techniques of our capnograph inventions referenced above. However, the optical stabilization technique of the present invention differs from that employed in our capnograph applications in that the filters of the present invention are not mounted on the detectors but rather in the "window" of the detector package which is inserted into the auditory canal. The attenuating filter is also placed so as to eliminate the thermal effects of the detector package itself. In other words, the attenuating filter of the invention is disposed such that the undesirable thermal effects caused by the detector device walls are effectively cancelled out. As will become more apparent from the following detailed description, this feature of the invention enables all undesirable infrared energy to be cancelled out and thus removed from the infrared energy detection.

In accordance with a preferred embodiment of the invention, an apparatus is provided for measuring the temperature of an infrared radiation emissive target, such as a tympanic membrane, comprising:

means for sensing the amount of incident infrared radiation emitted by the infrared radiation emissive target, comprising:

first and second thermopiles, connected in opposed relation to each other and positioned on the same substrate so as to receive incident infrared radiation emitted by the infrared radiation emissive target and by an ambient environment of the first and second thermopiles, for producing output electrical signals representative of the intensity of the incident infrared radiation, a bandpass filter, disposed in an energy path between the infrared radiation emissive target and the first and second thermopiles, for passing a predetermined range of infrared wavelengths of incident infrared radiation from the radiation emissive target to the first and second thermopiles; and an attenuating neutral density filter, disposed in the energy path so as to attenuate the incident infrared radiation impinging upon only one of the thermopiles from the radiation emissive target without attenuating incident infrared radiation in the energy path due to infrared emissions by the ambient environment of the first and second thermopiles; and means for processing the output electrical signals to determine the temperature of the radiation emissive target substantially independent of ambient temperature variations of the ambient environment.

In a preferred embodiment, a reference detector is also provided for detecting the ambient temperature of the ambient environment and generating a reference temperature signal which is processed with the output electrical signals by the processing means to determine an absolute temperature of the infrared radiation emissive target. Such processing means preferably comprises an amplifier for increasing the gain of the output electrical signals, a filter for eliminating noise in the output electrical signals, and a microprocessor for determining the temperature from the output electrical signals and the reference temperature signal. As would be apparent to one of ordinary skill in the art, the infrared radiation emissive target may be other internal tissues of a patient as well.

The arrangement of the invention may be incorporated into a noncontact infrared tympanic thermometer or a multifunction otoscope. Such devices also preferably include a display mounted on its housing for displaying the measured temperature. To facilitate such display, the device of the invention may include a tilt sensor for inverting the temperature display to read upright and left to right independent of the orientation of the device's housing. In addition, a speculum may be used for covering the end of the device's probe to prevent contamination of the directing means when the device is inserted into the patient's ear for the measurement of the amount of infrared radiation emitted by the patient's tympanic membrane. Also, the attenuating neutral density filter preferably has a transmission coefficient of approximately 0.50 in a preferred embodiment.

The invention also comprises a method of measuring the temperature of an infrared radiation emissive target, such as a tympanic membrane, comprising the steps of:

sensing the amount of incident infrared radiation emitted by the infrared radiation emissive target, comprising the steps of:

positioning first and second thermopiles in opposed relation to each other and on the same substrate so as to receive incident infrared radiation emitted by the infrared radiation emissive target and by an ambient environment of the first and second thermopiles, passing a predetermined range of infrared wavelengths of incident infrared radiation from the infrared radiation emissive target to the first and second thermopiles, attenuating the incident infrared radiation impinging upon only one of the first and second thermopiles from the radiation emissive target without attenuating incident infrared radiation received from the ambient environment of the first and second thermopiles, and producing output electrical signals representative of the intensity of the incident infrared radiation received by the first and second thermopiles; and processing the output electrical signals to determine the temperature of the radiation emissive target substantially independent of ambient temperature variations of the ambient environment.

Such a method in accordance with the invention preferably also comprises the further steps of detecting an ambient temperature, generating a reference temperature of the ambient environment signal corresponding to the detected ambient temperature, and processing the reference temperature signal with the output electrical signals to determine an absolute temperature of the infrared radiation emissive target. In addition, the processing step preferably comprises the steps of amplifying the output electrical signals so as to increase their gain, filtering the output electrical signals so as to eliminate noise, and determining the temperature from the output electrical signals and the reference temperature signal.

Preferably, the infrared radiation emissive target whose temperature is measured in accordance with the invention comprises an internal tissue of a patient and the positioning step includes the step of placing first and second thermopiles in a body cavity containing the internal tissue. In addition, when used in conjunction with a tympanic thermometer, the positioning step of the method of the invention may further include the step of placing a device housing the first and second thermopiles into the patient's ear canal. Also, the resulting temperature is preferably displayed on a temperature display. Such a displaying step may also comprise the step of inverting the temperature display to read upright and left to right independent of the orientation of a device housing the first and second thermopiles. Moreover, to prevent cross-contamination, the method of the invention may include the further step of covering the device housing the first and second thermopiles with a speculum before the device is inserted into the patient's ear for the measurement of the amount of infrared radiation emitted by the patient's tympanic membrane.

BRIEF DESCRIPTION OF THE DRAWINGS

The above and other objects and advantages of the present invention will become more apparent and more readily appreciated in the following description of presently preferred embodiments, taken in conjunction with the accompanying drawings, of which.

DETAILED DESCRIPTION OF THE PRESENTLY PREFERRED EMBODIMENTS

A device having the above-mentioned beneficial features in accordance with presently preferred exemplary embodiments of the invention will be described below with reference to FIGS. 1-3. It will be appreciated by those of ordinary skill in the art that the description given herein with respect to those figures is for exemplary purposes only and is not intended in any way to limit the scope of the invention. All questions regarding the scope of the invention may be resolved by referring to the appended claims.

Figure 1:
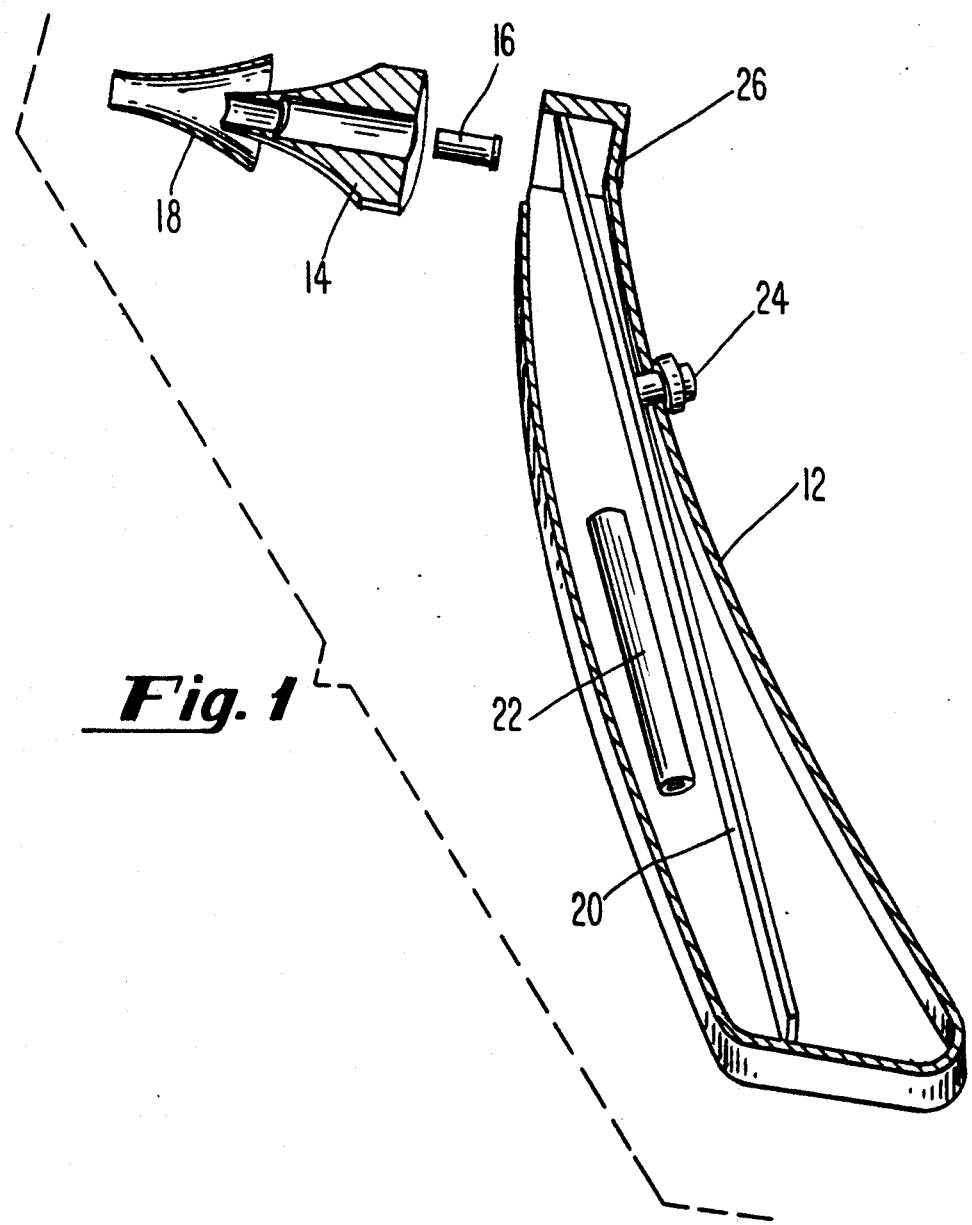
FIG. 1 illustrates a cutaway view of a noncontact infrared tympanic thermometer in accordance with the invention.

FIG. 1 illustrates a cutaway view of a noncontact infrared tympanic thermometer 10 in accordance with the invention. As shown, the tympanic thermometer 10 of the invention is similar in shape to an otoscope and is comprised primarily of a housing or body portion 12 (which is generally made of plastic or some other rigid material), a protruding probe portion 14 (preferably made of aluminum or plastic) for insertion into the patient's ear, an optically stabilized thermopile detector 16, and a disposable speculum 18 which is placed over the probe portion 14 before insertion of the probe portion 14 into the auditory canal for a temperature measurement. Within the housing 12 is preferably disposed a circuit board having a processing circuit 20 powered by a battery 22 upon depression of a button 24. The resulting temperature reading is preferably displayed on a digital display 26.

The tympanic thermometer 10 of the invention is preferably engineered to fit comfortably in the human hand. It is a single piece device with a temperature display 26 on one end and a curved design and tapered ear probe which make it easier to hold and aim at the tympanic membrane. The body of the device can be made small by incorporating "surface mount" electronic technology, and in a preferred embodiment, the ear piece of the invention can be made as small as 0.16 inches in diameter, the same size as a conventionally used 4 mm otoscope speculum.

Figure 2:
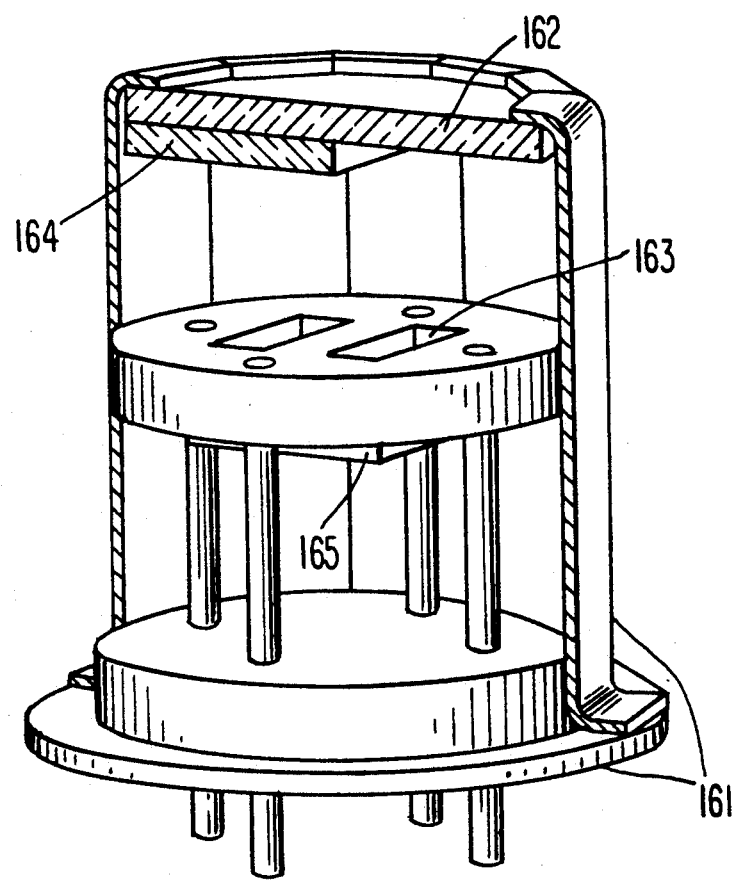
FIG. 2 illustrates a perspective side view of an optically stabilized detector for use in the tympanic thermometer of the invention.

FIG. 2 illustrates an optically stabilized infrared detector 16 in accordance with the invention. As shown, the optically stabilized detector 16 of the invention generally comprises a sensor housing 161 having disposed therein a bandpass filter 162, a two-channel thermopile detector 163, a neutral density filter 164 and a reference thermistor 165. The sensor housing 161 or "can" is designed to hold the detector circuitry in a predetermined relationship as will be described below. Bandpass filter 162 is designed to pass infrared wavelengths in a range of approximately 8-14 microns, which corresponds to emissions in the range of the internal temperature of a human being, for example. The two-channel thermopile detector 163 is preferably a pair of series opposed thermopile detectors of the type described in our U.S. application Ser. Nos. 07/401,952, 07/522,208 (U.S. Pat. No. 5,095,913) and 07/522,177 (U.S. Pat. No. 5,081,988), referenced above, the contents of which are hereby incorporated by reference as if set forth herein in their entirety.

Generally, the two-channel thermopile detector 163 in accordance with the invention comprises first and second series opposed thermopile detectors mounted on a common ceramic substrate as described in our aforementioned applications. As described therein, the individual thermopile detectors are formed by depositing a bi-metallic circuit upon a polyester film, such as Mylar, or another suitable substrate. Preferably, the thermocouples have a substrate thickness of approximately 1 mil. The thermopile detectors of the two-channel thermopile detector 163 are connected in series opposition so that the substraction of their outputs is inherent in their interconnection. The importance of this interconnection will be described more fully below.

The neutral density (attenuation) filter 164 of the detector 16 uniformly attenuates all wavelengths of energy which are incident upon it. In a preferred embodiment, the neutral density filter 164 may have a transmission coefficient of 0.50, but a transmission coefficient of 0 is also possible in accordance with the invention. Of course, one skilled in the art may use other neutral density filters with different transmission coefficients as desired. However, as will be apparent to one of ordinary skill in the art, the transmission coefficients preferably are not chosen to be close to 1.00 since that would inhibit operation of the detector. Generally, transmission coefficients of less than 0.75 are preferred. The neutral density filter 164 is placed within the housing 161 so as to overlap or "shadow" only one of the thermopile detectors of the two-channel thermopile detector 163 so that the received infrared radiation is only attenuated before impinging upon the "shadowed" detector. This enables a differential signal to be developed as will be described below.

Finally, reference thermistor 165 determines the ambient temperature of the detector 163 so that an absolute temperature measurement may be determined in accordance with known principles. This feature of the invention also will be described in more detail below.

The optically stabilized infrared detector 16 of the invention is unique in that the detector 16 is sensitive only to radiation from the target (the tympanic membrane) and not the side walls of the detector package. As a result, the device does not need to be maintained under isothermic conditions or repeatedly calibrated as in prior art devices. This selectivity of the invention is accomplished by locating the neutral density filter 164 over half of the optical aperture of the detector package. As shown in FIG. 2, the detector's active element consists of twop thermopile channels connected in series opposition such that any optical signal equally present in both channels will yield a zero net output. Signals that reach each detector substantially equally include the infrared energy emitted by the walls of the detector package 161. In a tympanic thermometer, the target temperature is typically 37° C., while the detector wall temperature varies from 20°-37° C. Because the two surfaces (the tympanic membrane and the detector wall) are at substantially the same temperature, emissions from the detector wall 161 that are not in some way eliminated from the measurement can cause large errors in the measured temperature, as recognized in the prior art.

The above problem is overcome in accordance with the invention because the infrared energy from the detector walls 161 falls substantially equally on the two thermopile channels and is thus cancelled by the series opposition connection. If it were not for the neutral density filter 164, infrared energy from the tympanic membrane would also fall equally on the two thermopile detectors and similarly cancel. However, the neutral density filter is aligned so that it "shadows" one of the detector channels as described above so that one detector receives less target energy than the other, thereby allowing a differential signal to be developed. This differential signal is then processed in order to determine the temperature as will be described below with reference to FIG. 3.

While there are other techniques for eliminating detector side wall emissions, such as controlling the side wall temperature and subtracting a constant from the signal as in the prior art, the present invention is more advanced because it allows "dynamic" elimination of the effect of the side wall emissions. Dynamic elimination is critical in situations where the detector side wall temperature changes, as is the case when the speculum of the tympanic thermometer is inserted into the auditory canal. At that time the detector begins a rapid transition from substantially room temperature to substantially body temperature. The present invention is designed such that this temperature transition does not adversely affect the temperature reading. This is so because the signals from any infrared emissions originating from behind the neutral density filter 164 in the sensor assembly are effectively canceled at the thermopile detectors as described above.

Thus, with the neutral density filter 164 in place and properly aligned and the two detector channels connected in series opposition, a signal will be developed as a result of infrared energy from the target, but none will result from detector package wall emissions. In general, no emissions occurring on the detector side (behind) the neutral density filter 164 will result in an output signal because there is no element to produce a differential signal. Only infrared emissions from in front of the filter 164 result in an electrical output signal because only those emissions pass through the neutral density element 164 which "shadows" one of the detector channels causing the differential signal at the detector. Accordingly, the neutral density filter 164 is preferably placed as close to the infrared energy source (tympanic membrane) as possible in order to cause cancellation of all undesired infrared emissions behind the neutral density filter 164.

In an alternate embodiment, the neutral density filter 164 can be placed in the speculum 18 so as to be as close as possible to the tympanic membrane. In such an embodiment, infrared emissions from the speculum itself as well as the detector walls, both of which are located behind the filter, can be cancelled so as to eliminate both sources of error. However, as shown in FIG. 2, in the presently preferred embodiment the neutral density filter 164 is placed within the housing 161 of the optically stabilized detector 16 since it is difficult to place the neutral density filter 164 on the speculum 18 without casting a "shadow" on both thermopile detectors 163. Of course, it is believed to be well within the skill of one of ordinary skill in the art to properly align a speculum having a neutral density filter 164 such that the "shadow" of the neutral density filter 164 only covers one of the thermopile detectors.

Figure 3:
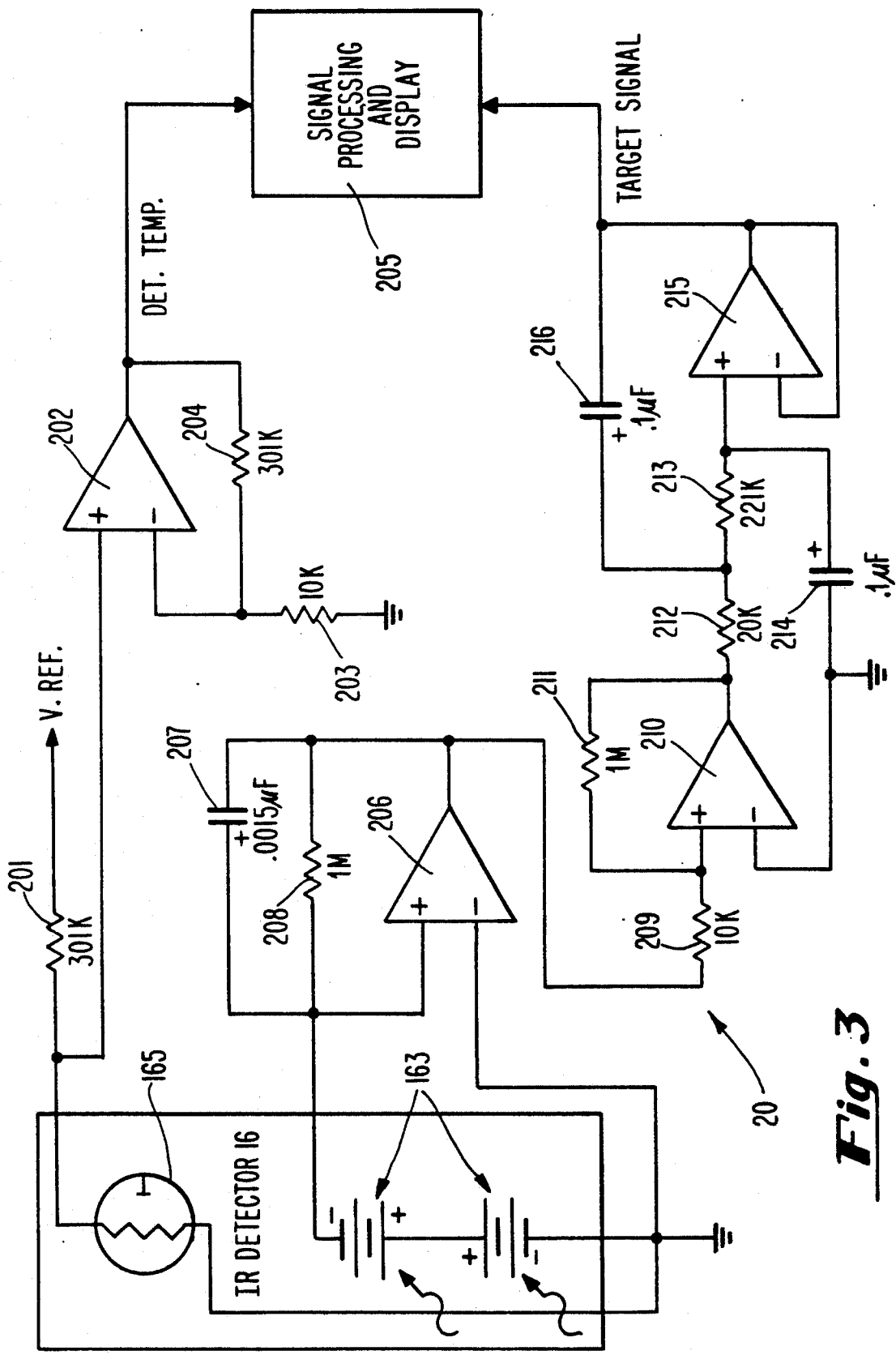
FIG. 3 illustrates a preferred embodiment of the processing circuit for processing the outputs of the optically stabilized detector and reference detector so as to produce a temperature signal.

FIG. 3 illustrates the interconnection of the thermopile detector 16 and the processing circuit 20 of the invention. As described above, the infrared detector 16 comprises thermopiles 163 which are connected series opposed. The received infrared radiation is received by these thermopile detectors 163 to create output signals. Also, the reference temperature of the detector 16 is determined by reference thermistor 165, and the output of the reference thermistor 165 is connected across resistor 201 to a voltage reference Vref and also applied to a positive input of an operational amplifier 202. A negative input of operational amplifier 202 receives a fed back output of operational amplifier 202 across resistors 203 and 204 as shown. The result is that the output of operational amplifier 202 is amplified so as to boost the signal gain of the output of reference thermistor 135 to a level which is acceptable by signal processing and display circuit 205. The detected reference temperature signal is therein processed as will be described below.

The series opposed outputs of thermopiles 163 are output to respective inputs of an operational amplifier 206. The output of a feedback network is also applied to the positive input of the operational amplifier 206, this network including a capacitor 207 and a resistor 208 which together provide a roll-off capacitance for rejecting high frequency noise. The output of operational amplifier 206 thus represents the difference signal between the respective detector outputs. This difference signal is applied across resistor 209 to a positive input terminal of operational amplifier 210. A feedback resistor 211 is also provided to connect the output of operational amplifier 210 to the positive input terminal of operational amplifier 210. The negative input terminal of operational amplifier 210 receives a feedback signal from a network comprising resistor 212, resistor 213 and capacitor 214 as shown. The output of resistor 213 is also applied to a positive input terminal of operational amplifier 215, and the output of operational amplifier 215 is fed back to the negative input terminal thereof as shown. Finally, a capacitance 216 connects the common node between resistors 212 and 213 to the output of operational amplifier 215 as shown. As would be apparent to one skilled in the art, the circuit comprising elements 209-216 functions as a low pass filter with a predetermined time constant. Preferably, the time constant is chosen to be on the order of the time response of the thermopile detector 163 so as to roll off high frequency noise such as the 60 Hz line frequency noise common in the United States. In a preferred embodiment of the invention, the resulting low pass filter has a 100 msec time constant. The resulting low pass filtered target signal is then applied to the signal processing and display circuit 205.

Signal processing and display circuit 205 processes the detected reference temperature and target signals in order to determine the absolute temperature of the tympanic membrane and hence the patient's internal temperature. The functions of signal processing and display circuit 205 may be programmed into a computer through software, such as a Mackintosh SE computer, but in a preferred embodiment of the invention, the signal processing and display circuit 205 may comprise a single chip microprocessor such as the Intel 8051 and an A/D converter such as the Analog Devices AD7824. Of course, other microprocessors and A/D converters may also be used in accordance with the invention.

As noted in the article by C. Hamel referenced above, the voltage output of a typical thin film thermopile detector directed at a target of temperature, $T_t$, may be simply determined in accordance with a known equation. In particular, signal processing and display circuit 205 processes the detected reference temperature signal ($T_a$) and the target temperature signal ($T_t$) in accordance with the following equation:

$$E_{out} = M(T_t^4 - T_a^4)$$

where:
$E_{out}$ = the detector output voltage;
$T_t$ = target temperature in degrees K;
$T_a$ = ambient temperature in degrees K; and $$M = \frac{z}{\pi} \frac{([A_t][A_d])}{D^2} R,$$

where:
$Z = 5.688 \times 10^{-2}$ W/cm$^2$/K (the Stefan-Boltzman constant);
II = a constant representative of the optical properties of the device (may be determined empirically);
$A_t$ = area of target in cm;
$A_d$ = area of detector element in cm;
D = distance from detector element to target; and
R = responsivity of detector in V/W, where typically R = 10 V/W.

From the foregoing equation, the target temperature $T_t$ in absolute terms is determined. The result is then displayed on display 26 (FIG. 1) in accordance with known techniques.

Thus, the present invention as configured in the preferred embodiments does not require environmental stabilization or waveguide temperature control as in the prior art because it utilizes an optically stabilized infrared detector 16. The optical stabilization technique in accordance with the invention renders the tympanic thermometer insensitive to ambient temperature effects and allows it to read true tympanic membrane temperatures. Moreover, by placing the optically stabilized detector 16 as close as possible to the end of the probe 18, all unwanted infrared emissions may be cancelled out.

Accordingly, the present invention is a significant improvement over prior art devices of its type in that the device is small enough to be placed inside the ear so as to eliminate the need for a waveguide and in that the device is constructed of two detector elements and a neutral density optical filter built into the window of the detector package so as to eliminate the sensing of emissions from the detector itself. The construction of the detector of the present invention thus allows it to be located inside the auditory canal, thereby removing the requirement for a waveguide to bring energy from the tympanic membrane to the detector. This eliminates the sensing of emissions from the waveguide and correction for this unwanted signal.

As would be apparent to one of ordinary skill in the art, the present invention need not use a closed end speculum cover 18. Rather, the speculum cover 18 of the invention may be similar to that used with conventional otoscopes whereby an opening is provided through which to "view" the tympanic membrane. It is accepted and understood that an open ended otoscope probe cover provides acceptable safety from cross contamination by extending sufficiently beyond the reusable parts to prevent patient contact. Also, the open ended probe cover design provides for minimal manufacturing cost and is presently preferred. On the other hand, as noted above, the speculum cover 18 may be modified such that the neutral density filter 164 is incorporated therein. Of course, such a speculum cover would not be open ended.

Although a number of exemplary embodiments of the invention have been described in detail above, those skilled in the art will readily appreciate that many additional modifications are possible in the exemplary embodiments without materially departing from the novel teachings and advantages of this invention. For example, the infrared detector of the invention may be incorporated into a conventional otoscope so that a multifunctional otoscope may be formed. Accordingly, all such modifications are intended to be included within the scope of this invention as defined in the following claims.

We claim:
1. An apparatus for measuring a temperature of an infrared radiation emissive target, comprising:
means for sensing the amount of incident infrared radiation emitted by said infrared radiation emissive target, comprising:
a substrate,
first and second thermopiles, connected in opposed relation to each other and positioned on the same said substrate so as to receive incident infrared radiation emitted by said infrared radiation emissive target and by an ambient environment of said first and second thermopiles, for producing output electrical signals representative of the intensity of said incident infrared radiation,
a bandpass filter, disposed in an energy path between said infrared radiation emissive target and said first and second thermopiles, for passing a predetermined range of infrared wavelengths of incident infrared radiation from said radiation emissive target to said first and second thermopiles, and an attenuating neutral density filter, disposed in said energy path so as to attenuate the incident infrared radiation impinging upon only one of said thermopiles from said radiation emissive target without attenuating incident infrared radiation in said energy path due to infrared emissions by said ambient environment of said first and second thermopiles; and means for processing said output electrical signals to determine said temperature of said radiation emissive target substantially independent of ambient temperature variations of said ambient environment.

2. An apparatus as in claim 1, further comprising a reference detector for detecting an ambient temperature of said ambient environment of said first and second thermopiles and generating a reference temperature signal, said reference temperature signal being processed with said output electrical signals by said processing means to determine an absolute temperature of said infrared radiation emissive target.

3. An apparatus as in claim 2, wherein said processing means comprises an amplifier for increasing the gain of said output electrical signals and a microprocessor for determining said temperature from said output electrical signals and said reference temperature signal.

4. An apparatus as in claim 1, wherein said infrared radiation emissive target comprises an internal tissue of a patient.

5. A tympanic thermometer for measuring the internal temperature of a patient's body from infrared radiation emitted by the patient's tympanic membrane, comprising:

a housing adapted for insertion into the patient's ear canal;

means within said housing for sensing the amount of infrared radiation emitted by the patient's tympanic membrane, comprising:

first and second thermopiles, connected in opposed relation to each other and positioned in said housing so as to receive infrared radiation emitted by the patient's tympanic membrane and by a portion of said housing in an energy path between the patient's tympanic membrane and said first and second thermopiles, for producing output electrical signals representative of the intensity of the radiation emitted by the patient's tympanic membrane, a bandpass filter, disposed in said energy path between the patient's tympanic membrane and said first and second thermopiles, for passing a predetermined range of infrared wavelengths of infrared radiation from the patient's tympanic membrane through said energy path to said first and second thermopiles, and an attenuating neutral density filter disposed at an end of said housing in said energy path between the patient's tympanic membrane and one of said first and second thermopiles so as to attenuate the infrared radiation from the patient's tympanic membrane which impinges upon said one thermopile without attenuating incident infrared radiation in said energy path due to infrared emissions by said portion of said housing in said energy path between the patient's tympanic membrane and said first and second thermopiles; and means for processing said output electrical signals to determine said temperature of the patient's tympanic membrane substantially independent of ambient temperature variations.

6. A thermometer as in claim 5, further comprising a reference detector for detecting an ambient temperature of said first and second thermopiles and generating a reference temperature signal, said reference temperature signal being processed with said output electrical signals by said processing means to determine an absolute temperature of the patient's tympanic membrane.

7. A thermometer as in claim 6, wherein said processing means comprises an amplifier for increasing the gain of said output electrical signals and a microprocessor for determining said temperature of the patient's tympanic membrane from said output electrical signals and said reference temperature signal.

8. A thermometer as in claim 5, further comprising a display mounted on said housing for displaying said temperature of the patient's tympanic membrane.

9. A thermometer as in claim 5, further comprising a speculum for covering said portion of said housing adapted for insertion into the patient's ear canal so as to prevent contamination of said housing when said thermometer is inserted into the patient's ear canal for the measurement of the amount of infrared radiation emitted by the patient's tympanic membrane.

10. A thermometer as in claim 5, wherein said attenuating neutral density filter has a transmission coefficient of approximately 0.50.

11. A method of measuring a temperature of an infrared radiation emissive target, comprising the steps of:

sensing the amount of incident infrared radiation emitted by said infrared radiation emissive target, comprising the steps of:

positioning first and second thermopiles in opposed relation to each other and on the same substrate so as to receive incident infrared radiation emitted by said infrared radiation emissive target and by an ambient environment of said first and second thermopiles, passing a predetermined range of infrared wavelengths of incident infrared radiation from said infrared radiation emissive target to said first and second thermopiles, attenuating the incident infrared radiation impinging upon only one of said first and second thermopiles from said radiation emissive target without attenuating incident infrared radiation received from said ambient environment of said first and second thermopiles; and producing output electrical signals representative of the intensity of said incident infrared radiation received by said first and second thermopiles; and processing said output electrical signals to determine said temperature of said radiation emissive target substantially independent of ambient temperature variations of said ambient environment.

12. A method as in claim 11, comprising the further steps of detecting an ambient temperature of said ambient environment of said first and second thermopiles, generating a reference temperature signal corresponding to the detected ambient temperature, and processing said reference temperature signal with said output electrical signals to determine an absolute temperature of said infrared radiation emissive target.

13. A method as in claim 12, wherein said processing step comprises the steps of amplifying said output electrical signals so as to increase the gain of said output electrical signals and determining said temperature from said output electrical signals and said reference temperature signal.

14. A method as in claim 11, wherein said infrared radiation emissive target comprises an internal tissue of a patient and said positioning step includes the step of placing said first and second thermopiles in a body cavity containing said internal tissue.

15. A method of measuring the internal temperature of a patient's body from infrared radiation emitted by the patient's tympanic membrane, comprising the steps of:

sensing the amount of incident infrared radiation emitted by the patient's tympanic membrane, comprising the steps of:
positioning first and second thermopiles in opposed relation to each other in a housing adapted for insertion in to the patient's ear canal and so as to receive incident infrared radiation emitted by the patient's tympanic membrane and by an ambient environment of said first and second thermopiles,
passing a predetermined range of infrared wavelengths of incident radiation from the patient's tympanic membrane to said first and second thermopiles,
attenuating, using an attenuating neutral density filter disposed at an end of said housing, the incident infrared radiation impinging upon only one of said first and second thermopiles from the patient's tympanic membrane without attenuating incident infrared radiation received from said ambient environment of said first and second thermopiles, and
producing output electrical signals representative of the intensity of said incident infrared radiation received by said first and second thermopiles; and
processing said output electrical signals to determine said temperature of the patient's tympanic membrane substantially independent of ambient temperature variations of said ambient environment.

16. A method as in claim 15, comprising the further steps of detecting an ambient temperature of said ambient environment of said first and second thermopiles, generating a reference temperature signal corresponding to the detected ambient temperature, and processing said reference temperature signal with said output electrical signals to determine an absolute temperature of the patient's tympanic membrane.

17. A method as in claim 15, wherein said processing step comprises the steps of amplifying said output electrical signals so as to increase the gain of said output electrical signals and determining said temperature from said output electrical signals and said reference temperature signal.

18. A method as in claim 15, wherein said positioning step includes the step of placing a device housing said first and second thermopiles into the patient's ear canal.

19. A method as in claim 15, comprising the further step of displaying said temperature on a temperature display.

20. A method as in claim 15, comprising the further step of covering a device housing said first and second thermopiles with a speculum to prevent contamination of said device when said device is inserted into the patient's ear canal for the measurement of the amount of infrared radiation emitted by the patient's tympanic membrane.

21. A tympanic thermometer for measuring the internal temperature of a patient's body from infrared radiation emitted by the patient's tympanic membrane, comprising:

a housing adapted for insertion into the patient's ear canal;
first and second thermopiles, connected in opposed relation to each other and positioned in said housing so as to receive infrared radiation emitted by the patient's tympanic membrane and by a portion of said housing in an energy path between the patient's tympanic membrane and said first and second thermopiles, for producing output electrical signals representative of the intensity of the radiation emitted by the patient's tympanic membrane;
a bandpass filter, disposed in said energy path between the patient's tympanic membrane and said first and second thermopiles, for passing a predetermined range of infrared wavelengths of infrared radiation from the patient's tympanic membrane through said energy path to said first and second thermopiles;
a speculum for covering said portion of said housing adapted for insertion into the patient's ear canal so as to prevent contamination of said housing when said thermometer is inserted into the patient's ear canal for the measurement of the amount of infrared radiation emitted by the patient's tympanic membrane, said speculum comprising an integral attenuating neutral density filter disposed in said energy path so as to attenuate the infrared radiation from the patient's tympanic membrane which impinges upon only one of said thermopiles; and
means for processing said output electrical signals to determine said temperature of the patient's tympanic membrane substantially independent of ambient temperature variations.

* * * * *

UNITED STATES PATENT AND TRADEMARK OFFICE
CERTIFICATE OF CORRECTION

PATENT NO. : 5,159,936

DATED : November 3, 1992

INVENTOR(S) : Yelderman et al.

It is certified that error appears in the above-identified patent and that said Letters Patent is hereby corrected as shown below:

Column 4, Line 43, before "07/401,952 change "No." to --Nos.--; after "(abandoned)" delete "." and add --and--.

Column 6, Line 59, after "temperature" add --of the ambient environment--.

Column 6, Line 60, after "ature" delete "of the ambient environment"

Column 8, Line 29, after "07/401,952" add --(abandoned)--.

Column 15, Line 24, after "insertion" change "in to" to --into--.

Signed and Sealed this

Twenty-eighth Day of December, 1993

*Attest:*

BRUCE LEHMAN

*Attesting Officer*   *Commissioner of Patents and Trademarks*